(12) United States Patent
Hafner et al.

(10) Patent No.: US 10,258,338 B2
(45) Date of Patent: Apr. 16, 2019

(54) ANASTOMOSIS INSTRUMENT WITH PIVOTABLE ANVIL

(71) Applicant: Aesculap AG, Tuttlingen (DE)

(72) Inventors: Nikolaus Hafner, Tuttlingen (DE); Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 656 days.

(21) Appl. No.: 14/437,589

(22) PCT Filed: Oct. 23, 2013

(86) PCT No.: PCT/EP2013/072157
§ 371 (c)(1),
(2) Date: Apr. 22, 2015

(87) PCT Pub. No.: WO2014/067829
PCT Pub. Date: May 8, 2014

(65) Prior Publication Data
US 2015/0297237 A1 Oct. 22, 2015

(30) Foreign Application Priority Data
Oct. 29, 2012 (DE) .......... 10 2012 110 312

(51) Int. Cl.
*A61B 17/11* (2006.01)
*A61B 17/115* (2006.01)
(Continued)

(52) U.S. Cl.
CPC ....... *A61B 17/1114* (2013.01); *A61B 17/1155* (2013.01); *A61B 18/148* (2013.01);
(Continued)

(58) Field of Classification Search
CPC ............. A61B 17/1114; A61B 17/1155; A61B 18/1445; A61B 18/148;
(Continued)

(56) References Cited

U.S. PATENT DOCUMENTS

| 4,566,620 A | 1/1986 | Green |
| 5,403,312 A * | 4/1995 | Yates ............... A61B 17/07207 |
| | | 606/142 |

(Continued)

FOREIGN PATENT DOCUMENTS

| CN | 2383476 Y | 6/2000 |
| CN | 102711646 A | 10/2012 |

(Continued)

OTHER PUBLICATIONS

First Chinese Office Action for Chinese Application No. 201380056956.7, dated Nov. 17, 2016, 7 pages.

(Continued)

*Primary Examiner* — Michael F Peffley
(74) *Attorney, Agent, or Firm* — RatnerPrestia

(57) ABSTRACT

An anastomosis instrument includes a headpiece shaft which can be inserted in an instrument shaft so as to be axially shiftable therein, a plate-like and/or anvil-like headpiece being axially shiftable on the distal end portion of the headpiece shaft and being supported via a cross pin between a processing position and a withdrawal position, the headpiece on the headpiece shaft being displaced or shifted from a first, proximally retracted latching position in which the headpiece shaft is coupled to the headpiece in a form-fitting manner to fix the headpiece in the processing position so that it is unable to pivot, to a second, distally advanced latching position in which the form fit is released in order to allow the headpiece to swivel to the withdrawal position.

11 Claims, 2 Drawing Sheets

(51) Int. Cl.
*A61B 18/14* (2006.01)
*A61B 18/00* (2006.01)
*A61B 17/00* (2006.01)
*A61B 17/072* (2006.01)

(52) U.S. Cl.
CPC .............. *A61B 18/1445* (2013.01); *A61B 2017/00367* (2013.01); *A61B 2017/07257* (2013.01); *A61B 2017/1132* (2013.01); *A61B 2018/0063* (2013.01); *A61B 2018/00619* (2013.01); *A61B 2018/142* (2013.01)

(58) Field of Classification Search
CPC .......... A61B 2017/00367; A61B 2017/07257; A61B 2017/1132; A61B 2018/00619; A61B 2018/0063; A61B 2018/142
See application file for complete search history.

(56) References Cited

U.S. PATENT DOCUMENTS

| | | | | |
|---|---|---|---|---|
| 5,588,579 | A | * | 12/1996 | Schnut ................. A61B 17/115 227/175.1 |
| 6,957,758 | B2 | * | 10/2005 | Aranyi ................. A61B 17/072 227/176.1 |
| 7,303,106 | B2 | * | 12/2007 | Milliman ............. A61B 17/115 227/175.1 |
| 8,540,132 | B2 | | 9/2013 | Marczyk et al. |
| 9,138,231 | B2 | | 9/2015 | Weisshaupt et al. |
| 2008/0230581 | A1 | * | 9/2008 | Marczyk ............. A61B 17/115 227/176.1 |
| 2012/0325888 | A1 | | 12/2012 | Qiao |
| 2013/0035683 | A1 | * | 2/2013 | Weisshaupt ........ A61B 17/0643 606/37 |
| 2013/0092720 | A1 | * | 4/2013 | Williams ............ A61B 17/1155 227/181.1 |

FOREIGN PATENT DOCUMENTS

| | | |
|---|---|---|
| DE | 202010013151 | 3/2011 |
| DE | 202012100197 | 4/2012 |
| EP | 0698376 | 2/1996 |
| EP | 1857058 | 12/2009 |
| EP | 1680028 | 1/2012 |
| GB | 2182882 B | 4/1986 |
| JP | S61501826 A | 8/1986 |
| JP | H07171159 A | 7/1995 |
| JP | H0866406 A | 3/1996 |
| JP | 2007307364 A | 11/2007 |
| WO | 2004032766 A2 | 4/2004 |
| WO | 2011109988 | 9/2011 |

OTHER PUBLICATIONS

German Search Report for German Application No. 10 2012 110 312.7 dated Aug. 12, 2013, including partial English translation.
International Search Report dated Jan. 27, 2014 for International Application No. PCT/EP2013/072157.
Notification of Reasons for Rejection for Japanese Application No. 2015-538429, dated Aug. 8, 2017, including English translation, 11 pages.

* cited by examiner

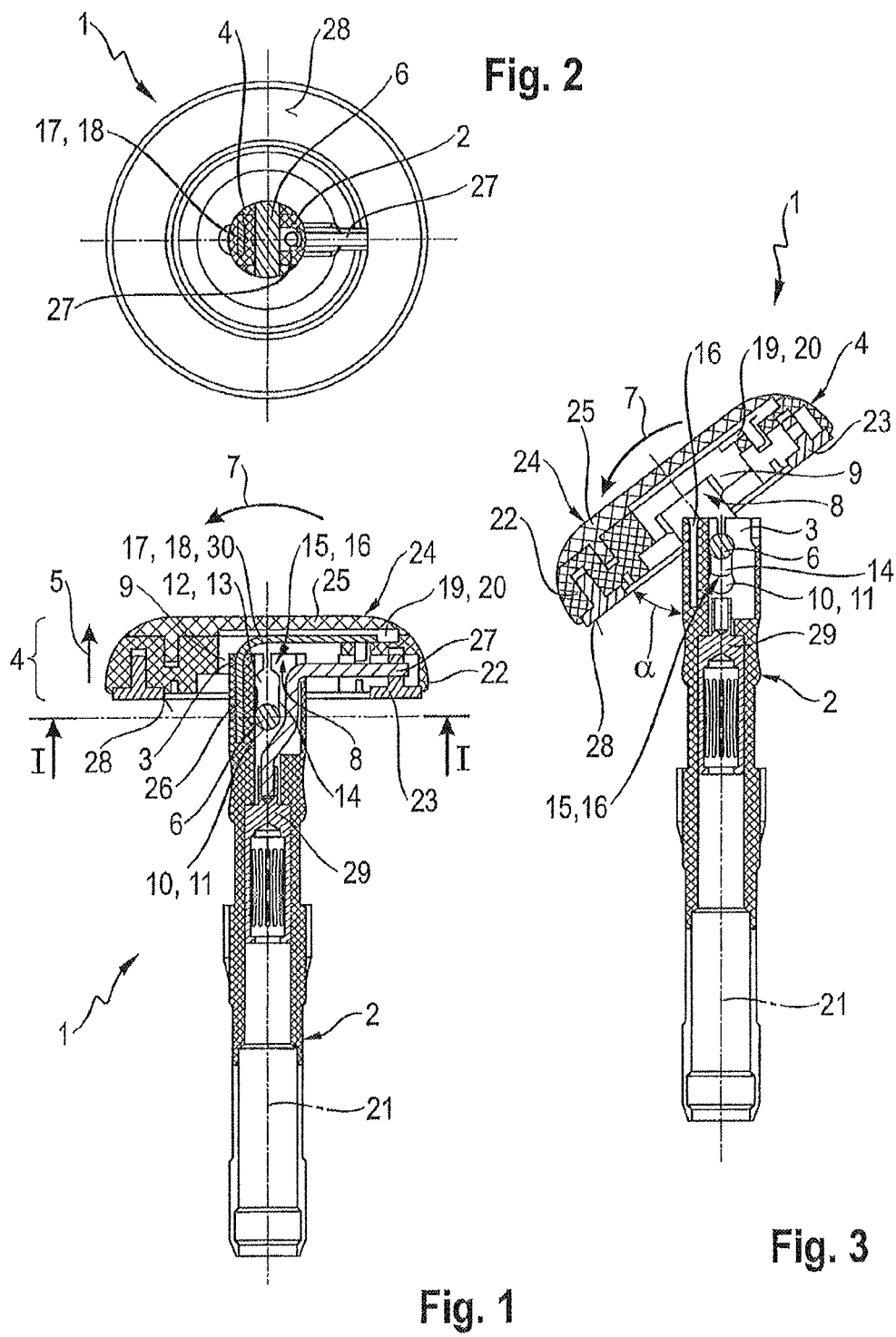

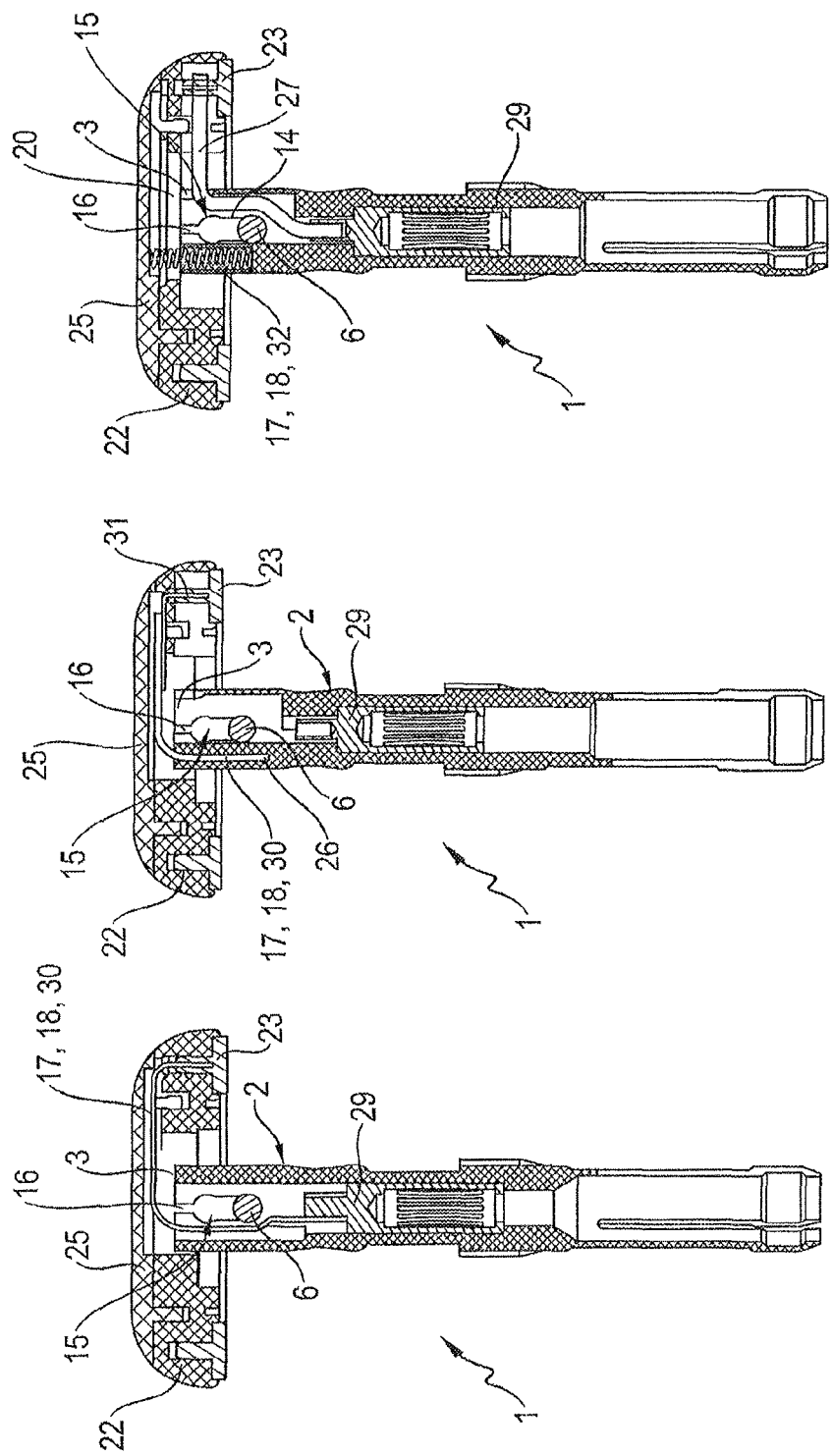

ANASTOMOSIS INSTRUMENT WITH PIVOTABLE ANVIL

RELATED APPLICATIONS

This is the United States national entry of International Application No. PCT/EP2013/072157, filed Oct. 23, 2013, which claims the benefit of priority of German Application No. DE 10 2012 110 312.7, filed Oct. 29, 2012. The contents of International Application No. PCT/EP2013/072157 and German Application No. DE 10 2012 110 312.7 are incorporated by reference herein in their entirety.

FIELD

The invention relates generally to a surgical instrument which is suited for the preparation of an anastomosis and more specifically to a surgical instrument that comprises a headpiece shaft which can be inserted in an instrument shaft so as to be axially shiftable therein, a plate-like and/or anvil-like headpiece being axially moveable on the distal end portion of the headpiece shaft and being supported via a cross pin between a processing position and a withdrawal position.

The headpiece may also be referred to as an anvil, and the headpiece shaft may be referred to as a head shaft, center rod or center bar.

BACKGROUND

Anastomosis instruments of this type are known from EP 1 857 058 B1, for example. This document discloses an inclination-type anvil assembly which is suitable for being used with a circular anastomosis clip setting device. Said device comprises a center bar, a head assembly (anvil) comprising a housing, a shoulder, an anvil plate including clip deformation dents and a cutting ring supporting element. Here, the head assembly is pivotally fastened to the center bar and can be swiveled with respect to the center bar between a non-angled position perpendicular to the axis of the center bar and an angled position. The cutting ring supporting element is positioned so as to surround the shoulder and is moved along the shoulder from a first position in which a portion of the supporting element is positioned to prevent the head assembly from carrying out a swivel motion from the non-angled position to the angled position, to a second position in which the supporting element is positioned to allow a swivel motion of the head assembly with respect to the center bar from the non-swiveled position to the swiveled position, if the clip device is triggered. The head assembly further comprises a lock element which is positioned to prevent a backward motion of the supporting element from the second position to the first position, the lock element being in particular a pivoting cam lock element. Such a device is used for the preparation of a surgical end-to-end anastomosis, for instance. It goes without saying that such an instrument can also be used for side-to-side-anastomoses, side-to-end anastomoses and end-to-side anastomoses, in particular in the stomach, esophagus and bowel zones.

Regarding elaborate hand-made sutures used for connecting two parts of the bowel, for example, the instrument according to EP 1 857 058 B1 can be used as an alternative circular clip suture instrument.

With such clip suture instruments, the anvil is axially pressed against a clip magazine at the front side, with body tissue being clamped therebetween. Next, clips are stuck through the clamped tissue, for instance through the bowel, and are deformed on the anvil (or on the cutting ring supporting element), so that an axial connection between two hose-like ends of the bowel is produced. In order to restore the continuity of the hollow organ, the axial passage in the clip area is stamped out with a round blade (annular ring blade), for instance; in this process, the anvil serves as an axial counter bearing for the circular blade supported in the clip magazine.

During removal of the instrument, i.e. when the anvil is pulled (retracted/removed) through the clip suture, the connected bowel areas must not be stretched too much, as this could result in a damage of the clip suture produced immediately beforehand. This is why the anvil is tilted/pivoted by means of a spring mechanism after the clipping process in many cases. The anvil or the headpiece is supported via a headpiece shaft, a center rod or a center bar and is moved to a removal position in said case of actuation. This removal position may also be referred to as a withdrawal position. In this removal posture/position, the anastomosis instrument or the anvil (the headpiece) has a smaller projected area than in the processing position (as seen in the longitudinal direction of the instrument). The tilting operation is usually activated by the feed motion of the blade, in most cases by permanently deforming, i.e. partially destroying a retaining element such as a deformable disk.

Due to tilting the headpiece (anvil/anvil head), the circumference as seen in the direction of the longitudinal axis of the instrument is reduced by such an extent, that the set clip rows are not overstretched during the removal of the instrument. The risk of a leakage of the anastomosis is reduced due to the tiltable anvil having been transferred to the withdrawal position, as the mechanical stressing of the suture is significantly lower during removal of the instrument.

The tissue is locally perforated with the known instruments using mechanical clips as well as with a manual hand-made suture. These perforations are potential places for leakage and represent spots which are prone to inflammations. It is vital to avoid such a situation with an anastomosis instrument in the future.

The prior art, for instance the document DE 20 2010 013 151 U1, shows a surgical system which is improved in this respect and intended for connecting body tissue, comprising a surgical instrument including a connection device for connecting body tissue. Here, the connection device comprises two tool elements which can be moved relative to each other. The instrument further comprises a cutting device comprising a cutting element for the severing of tissue, the cutting element being arranged so as to be movable relative to at least one of the tool elements. The cutting element has a cutting edge defining a cutting plane which is inclined relative to a longitudinal axis defined by the instrument in the area of the connection device. This surgical system uses a high-frequency cutting device (HF cutting device) acting with electrical current. Monopolar and bipolar cutting devices are disclosed here as well.

This system allows to do without any clips, so that the so-called "Tissue Fusion Technology" (TFT) can be applied. Here, different or also identical tissue types are connected to each other by the use of HF energy, preferably in bipolar fashion. As in this technology the tissue layers are not connected to each other by clips, it is also advantageous here if only small forces act on the anastomosis/anastomosis suture during the removal of the anastomosis instrument.

Here too, tiltable electrode plates are provided to avoid any damage of the anastomosis during pulling out the instrument.

Unfortunately, the instruments known from prior art for tilting the headpiece (anvil) usually are not designed to be reversible, so that a quick and easy re-employment of one and the same instrument in the context of a medical treatment or on the human body is not possible. Here, it is necessary to provide an improvement. In addition, up to now there is no possibility to determine whether the tilting operation has been carried out in a correct manner, i.e. if the headpiece has been properly transferred to the removal position.

SUMMARY

Therefore, it is the object of the invention to change this situation and preferably to provide a feedback to the surgeon.

As the instruments known hitherto include an elaborate mechanical system and use a very high number of components, the manufacturing, possibly the cleaning, the maintenance and the operation are very expensive and imply significant costs. An improvement is to be achieved in this respect as well.

As a last point, the process of transferring the headpiece to a removal position is supposed to occur in a controlled manner so as to reduce the forces which act on the sealed area present on the hollow organ and are produced during the removal of the headpiece.

This object is achieved in general by an anastomosis instrument according to the invention, and in particular by the fact that the headpiece (the anvil) on its headpiece shaft is (or can be) displaced or translated from a first, proximally retracted latching position in which the headpiece shaft is coupled to the headpiece in a form-fitting manner to fix the headpiece in the processing position so that it is unable to pivot, to a second, distally advanced latching position in which the form fit is released (unlocked/canceled) in order to allow the headpiece to swivel (turn/rotate/tilt) about a hinge or joint to the withdrawal position (withdrawal posture). In the processing position (processing posture), a process is carried out in terms of a connecting processing of two parts of the hollow organ (bowel), for instance by making use of clips and/or electricity (HF). In the withdrawal position, the anastomosis instrument is pivoted to such an extent that it can be removed from the hollow organ almost without any resistance.

Thus, upon releasing a latching or locking means, the headpiece can be moved relative to the headpiece shaft to a state in which a pivoting movement can be achieved, for instance in automatic fashion by means of a pretensioned spring. If the headpiece has been displaced or moved to the second, distally advanced latching position, for example by the impact of a knife (such as a circular blade) or by the intentional actuation of the shaft beyond a predefined resistance, the headpiece swivels in a self-acting fashion, almost automatically from the processing position to the withdrawal position as soon as the instrument has again been opened to a sufficient extent. If the headpiece is in the withdrawal position, its proximal end—which is provided with optional pockets for receiving clips or (alternatively or cumulatively) with one or more electrodes—is situated in a plane which is crossed by the longitudinal axis of the headpiece shaft, namely in a (pre-)defined angle α.

If the headpiece is transferred from the first latching position in which the form fit between the headpiece and the headpiece shaft is present such that swiveling the headpiece (about a swivel axis protruding transverse to/perpendicular to the longitudinal axis) relative to the headpiece shaft is not possible, to a second latching position which is further away as seen in the distal direction, pivoting will be allowed. The form fit which was previously present between the headpiece and the headpiece shaft now does not exist any more. The process of pulling out or pushing out the headpiece from the headpiece shaft ensures the transfer of the headpiece to this initial position required for swiveling.

Hence, the forces are reduced which act on the sealed surface in the bowel area and are produced during retracting the headpiece (for instance by an electrode plate) out of the hollow organ. The swiveling of the headpiece can be performed in a controlled manner, and the removal of the anastomosis instrument from the hollow organ (for instance the bowel) can be carried out in a controlled manner as well.

In summary, the gist of the present invention relates to a pivoting mechanism for the anvil of a bipolar anastomosis instrument. According to the invention, the pivoting mechanism provides two motion patterns which are uncoupled from each other: First, the anvil can be axially shifted with respect to a headpiece shaft, in order to be moved from a proximally retracted position in which a form fit connection supports the anvil in a rigid manner on the headpiece shaft, to a distally advanced position in which the form fit connection is released. Further, the anvil is supported on the headpiece shaft in a pivotable manner exclusively in the distally advanced position with respect to the headpiece shaft.

Advantageous exemplary embodiments are explained in more detail below.

Thus, it is advantageous if the headpiece comprises an electrode on its proximal side facing the headpiece shaft; it is preferred that this electrode is mounted in an electrode plate and has a ring-shaped design and/or if a plurality of pockets for the processing/bending of clips is provided. In this arrangement, the electrode(s) may form the pockets. In this case, the pockets are formed into chambers which are entered by the clips and where the clips are bent. In this way, it is possible to achieve the connection of the tissue parts of the bowel with the help of clips; another possibility is to omit the clips and to realize the connection only via the welding effect of the electricity applied via the electrode. It is also conceivable to combine these two possibilities.

It is expedient if a cross pin forming the headpiece hinge is shiftable guided in a longitudinal slit in the headpiece shaft so as to be able to be moved back and forth between the two latching positions. In this case, the longitudinal slit functions as a guide/slot-type guide, with the option that the longitudinal slit extends up to the distal end of the headpiece shaft, is open at the end face and in this way ensures a resilient spring fork-shaped design of the headpiece shaft in the area of the guide (in the transverse direction/in the radial direction).

Here, it is advantageous if the headpiece shaft is constructed to be resilient in the area of the longitudinal slit in the transverse direction, as this measure allows to retain the cross pin for instance in a first transverse hole (1st latching position in the longitudinal slit) and to transfer it—only after a spreading of the headpiece shaft—to a second transverse hole (2nd latching position in the longitudinal slit) which is closer to the distal end as seen from the first transverse hole. This means that a resistance has to be overcome in a decided manner, so that the cross pin can move from its first latching position to its second latching position. To this end, a force should be exerted which is somewhat higher than that which exists during the normal use of the instrument in its processing position. In other words, the force required to shift the cross pin from its first latching position contrary to the spring force of the slotted headpiece shaft should be larger than all those forces which act on the cross pin during the standard use of the instrument. Any unintentional jumping of the cross pin from the first latching position to the second latching position can be avoided by this measure. This prevents the headpiece/anvil from any unintentional tilting/swiveling. It goes without saying that the triggering force can also be set so as to be smaller than the maximum processing forces which are to be expected. In this case, triggering the first latching position is already aimed at in the standard operation (that force which is known to be required for a sufficient welding of the tissue by coagulation), in order to allow for the removal of the instrument immediately upon completing the tissue welding process.

In this case, it is advantageous if the headpiece—in the second, distally advanced latching position—can be swiveled about the cross pin (which is preferably aligned so as to be orthogonal to the longitudinal axis of the headpiece) into the withdrawal position. The cross pin may then serve as a pivot bearing to let the headpiece rotate when the form fit in the first latching position between the outer side of the headpiece shaft and an inner side of the headpiece does not exist any more.

It is also expedient if a spring element such as a mechanical spring is attached to the headpiece and the headpiece shaft, as appropriate, in such a manner that a swiveling of the headpiece is enforced when the headpiece is dislocated from the first latching position to the second latching position. A sort of automatic system can then be realized, so that, when the headpiece has been transferred to the position which is further away as seen in the distal direction (the cross pin is then in the second latching position), a tilting or swiveling of the headpiece into the withdrawal position can occur in a self-acting manner.

In terms of mechanical circumstances, it has turned out to be particularly reasonable and easy to mount if the spring is eccentrically supported in the headpiece shaft, i.e. so as to be transversely spaced from the longitudinal axis of the headpiece shaft (preferably orthogonally spaced from the longitudinal axis of the headpiece shaft), so that the longitudinal slit can be centrally arranged. This also allows the headpiece to have a symmetric design.

Further, if the spring is shiftably supported in the headpiece or in the headpiece shaft, preferably in a shaft-like recess or a similar cavity, the spring does not impede the axial shifting of the headpiece from the first latching position to the second latching position with a simultaneous pivoting of the headpiece about the pin, triggered by the (bendable) spring.

An advantageous exemplary embodiment is also characterized in that the spring is implemented as a leaf spring, leg spring or compression spring (such as a coil spring), said spring preferably having a state of smaller tension in the withdrawal position than in the processing position; more preferably, the spring is substantially relaxed in the withdrawal position.

For the purpose of avoiding an unintentional triggering, i.e. swiveling of the headpiece shaft, it is advantageous if the cross pin and the longitudinal slit are matched with each other such that a predetermined resistance has to be overcome during transferring the headpiece from the first latching position to the second latching position; it is further preferred that the force for overcoming the resistance is larger than the force which exists with a normal actuation of the anastomosis instrument which does not cause the headpiece to fold down, such as during cutting through tissue with a knife integrated in the instrument or during a displacement of the headpiece shaft for adapting the instrument to the thickness of the tissue to be treated as well as for applying pressure onto the patient's tissue during feeding electrical energy and/or setting clips.

Further, it is advantageous if the electrode is electrically contacted by means of the spring (e.g. by means of the leaf spring). In addition or as an alternative, a strand may also be used for providing the electrical contacting.

In other words, a tiltable electrode plate (headpiece/anvil) is basically presented, comprising a shaft for being received in the shaft of an anastomosis instrument. The headpiece shaft, being supported in the instrument shaft so as to be longitudinally shiftable therein, has its distal end portion provided with two transverse through holes which are arranged one above the other and are connected through a narrowed intermediate area. Above the upper hole, the headpiece shaft is also designed to be slotted/forked. Here, reference is made to the fact that it is not absolutely necessary to give the end side of the headpiece shaft a forked design; rather, it may also have a closed end side, i.e. the longitudinal slit does not have an open end face, but a closed one. In this case, the shaft material (for instance PEEK) has to have a sufficient elasticity to allow a radial spreading of the slot by the cross pin during its longitudinal displacement.

In the basic position, i.e. the processing position, the shaft is arranged at right angles to the electrode plate. In this position, tilting the electrode plate is not possible due to the form fit between the electrode plate and the distal end of the headpiece shaft, as the headpiece shaft rests against the electrode plate such that it is not able to perform a rotation or relative pivot motion.

If a predetermined force is applied in the axial direction of the headpiece shaft, it will move along in the same direction. In doing so, the cross pin will snap in place in the second hole above the first one. In this second position, the electrode plate can be rotated. Due to the influence of a spring force, for instance, the electrode plate is tilted and transferred to the withdrawal position as soon as the instrument has again been opened to a sufficiently large extent (cf. clip suture instruments).

Here, the spring force may be applied by a leaf spring, a leg spring or a compression spring. If the design is realized with a leaf spring, it is in particular conceivable to contact the electrode with the aid of said leaf spring.

Further, it is suggested to realize the tilting mechanism not by pulling out the shaft, but to trigger it by advancing the blade. Apart from the solution illustrated below including a double hole, other designs such as those comprising an elongated hole, a conically narrowing hole or a (different) snap connection are conceivable. The already presented solutions are conceivable both for clip suture instruments and any other instruments for the preparation of an anastomosis and can be applied in particular with respect to TFT.

A bipolar design is just as possible as a monopolar design, i.e. making use of a cell-connecting impact on the hollow organ without a counter-electrode. The result is a circular sealing instrument with a particularly high efficiency. Here, the electrode plate itself may be formed as an anvil which could also be used for the deformation of the clips. It is remarkable that this anvil construction allows the tilting by pulling out the headpiece shaft. In combination with the double hole in the narrowed zone, the concept provides a particularly efficient solution for the mentioned problem regarding a tiltable anvil or a tiltable electrode plate. In the context of the present invention, the tissue will not be perforated if the anastomosis instrument is used exclusively in the course of a high-frequency sealing, but is extensively sealed in a tight manner. Thus, the risk of a leakage is smaller or practically eliminated.

Further, the tilting process can be reversed by a simple click-in process of the headpiece shaft, i.e. the achievement of a snap connection. The cross pin will again snap in place in its first, proximal latching position. This is accompanied by the form fit between the headpiece and the headpiece shaft being re-established. This may be advantageous if the electrode plate should be slightly angled for the purpose of an easier insertion and only then is to be transferred to its basic position, i.e. the processing position. Minimally invasive operations such as those in which the electrode plate is transorally inserted, represent an example for this. Here, it is referred to the fact that such a form fit can be established in a simple manner in that an axial hole or an axial sleeve is formed in the electrode plate/anvil on the side facing its shaft and serves for receiving the headpiece shaft.

The tilting process cannot only be triggered by pulling out the body shaft, but alternatively or in addition may (also) be brought about by advancing a blade, in particular a blade having a circular cross-section. A peeling effect occurring in the tilting process may be advantageous if it comes to any tissue adherences between the electrodes.

The solutions illustrated below are also conceivable especially with clip suture instruments or other instruments for the preparation of an anastomosis.

BRIEF DESCRIPTION OF THE DRAWING FIGURES

Various embodiments of an anastomosis instrument according to the invention are explained in more detail below and illustrated in the drawings in which:

FIG. 1 shows a first embodiment of a detail of an anvil/anvil assembly of an anastomosis instrument in a partial longitudinal section in a processing position, using a strand for delivering current to an electrode, FIG. 2 shows a cross-section through the headpiece shaft of the anvil assembly of the anastomosis instrument of FIG. 1 along line I, FIG. 3 shows the detail of the anvil assembly of the anastomosis instrument illustrated in FIG. 1 with the headpiece being in a withdrawal position/removal position (the strand and the leaf spring are not illustrated here), FIG. 4 illustrates, in a manner comparable to FIG. 1, a second embodiment of the anvil assembly of an anastomosis instrument in which a leaf spring is used for directly contacting the electrode and a strand is omitted, FIG. 5 shows a third embodiment of the anvil assembly of an anastomosis instrument which is represented in a processing position similar to the variations illustrated in FIGS. 1 and 4, two leaf springs being used and a strand being omitted, and FIG. 6 shows a fourth embodiment of the anvil assembly of an anastomosis instrument in a processing position, a compression spring acting in the axial direction being used instead of one or more leaf springs, and a strand for contacting the electrode being additionally provided.

The Figures are merely of schematic nature and only serve for the understanding of the invention. The same elements are provided with the same reference numerals.

DETAILED DESCRIPTION

FIG. 1 illustrates a first embodiment of an anvil assembly 1, according to the invention, of an anastomosis instrument in the area of its distal end portion. The anastomosis instrument consequently comprises a headpiece 4 which can be inserted or is inserted so as to be axially shiftable at the distal end of an instrument shaft (not shown in further detail). In particular, the instrument's headpiece 4 is inserted, by means of its own headpiece shaft 2, in the instrument shaft (at its distal end) in an axially shiftable manner, with the instrument shaft also comprising a handle piece at its opposite proximal end in order to actuate individual functional units of the anastomosis instrument. Together with the headpiece 4, the headpiece shaft 2 forms a kind of mushroom consisting of the cap (headpiece 4) and the stem (headpiece shaft 2) which engage each other. Specifically, a distal end portion 3 of the headpiece shaft 2 is inserted, in a processing position illustrated in FIG. 1, in the plate-like or anvil-like headpiece 4 on its underside. Here, the headpiece 4 is supported on the headpiece shaft 2 so as to be axially shiftable in the longitudinal direction (and tiltable as well), as will be described in more detail below. The headpiece 4 as a whole may also be referred to as an anvil. The headpiece 4 is supported in the headpiece shaft 3 so as to be axially shiftable along the arrow 5 via a mechanical system described in the following.

The headpiece 4 comprises an axially protruding mount/pivot bearing (not shown in more detail in the Figures) on its (flat) underside facing the distal end face of the headpiece shaft 2, in which a transverse pivot bolt or cross pin 6 is received. Hence, the cross pin 6 is oriented so as to be substantially parallel to the underside of the headpiece 4 and also spaced therefrom.

On the underside of the headpiece 4 as well as with a vertical distance to the cross pin 6 (i.e. directly above the cross pin 6), there is formed a kind of seating 8 for the distal end portion 3 of the headpiece shaft 4; the end portion 3 can be inserted or plugged into said seating so as be axially shiftable but unable to pivot.

Hence, if the headpiece 4 is moved away from the headpiece shaft 2 distally in the direction of the arrow 5, so that its distal end portion slides out of the seating, it is able to perform a swivel motion about the cross pin 6 in the direction of the arrow 7 in the presence of a correspondingly sufficient distance. The headpiece 4 will then arrive at its withdrawal position illustrated in FIG. 3.

In the processing position, a form-fit exists between the radial outer side of the distal end portion 3 and an inner side of the seating or recess 8 in the area of a shoulder 9 formed on the seating 8, said form-fit saving or preventing the headpiece 4 from performing a swivel motion in the direction of the arrow 7. The headpiece 4 may have its recess 8 provided with an (axial) toothing such as a spline profile. The distal end 3 of the headpiece shaft 2, i.e. the end facing the headpiece 4, may be provided with a matching external toothing similar to a spline shaft. It is also possible to provide side face geometries which have an involute shape.

Here, the cross pin 6 is located in a headpiece shaft side (transverse) opening 10 which may be implemented as a first transverse through hole 11 at the distal end portion 3. This first transverse hole 11 is arranged to be further away from the distal end face of the headpiece shaft 3 than a further (transverse) opening 12 which is formed as a second transverse through hole 13. The first transverse hole 11 and the second transverse hole 13 extend parallel to each other and perpendicular to the longitudinal axis 21 of the headpiece shaft 2 and so as to completely penetrate the headpiece shaft 2.

The two openings 10 and 12 are spaced from each other via a narrowing zone/stretching zone 14. These two openings 10 and 12, i.e. the first and second transverse holes 11 and 13 as well as the narrowing zone/the zone of enhanced resistance/the stretching zone 14 are part of an inner (slot-type) guide 15 which in the present case is implemented as a straight longitudinal slit 16 on the distal end portion 3 of the headpiece shaft 2. The longitudinal slit 16 extends up to the distal end face, i.e. it divides the headpiece shaft 2 in two partial hollow cylinders (longitudinal forks of the shaft) which can move apart from each other in springy/elastic fashion, with the first transverse hole 11 constituting the proximal termination of the longitudinal slit 16 and the second transverse hole 12 being positioned axially in front of the distal end face of the headpiece shaft 2 and hence in front of the distal end of the longitudinal slit 16. The longitudinal slit 16 may have a straight or curved shape or it may comprise curved portions. It may also be based on a screw shape. It is not absolutely necessary that the longitudinal slit extends up to the distal end of the headpiece shaft.

A spring element 17 is formed in the manner of a mechanical spring 18, in the present case in particular as a leaf spring (which is straight when relaxed), e.g. as a leaf spring 30 (see FIGS. 1, 4 and 5) or 31 (see FIG. 5).

The leaf spring 30 illustrated in FIG. 1 is inserted in a non-shiftable manner in an axial groove formed in the wall of the headpiece shaft 2 and extends in a recess or groove 19, formed by means of a cavity 20, into the headpiece 4. As illustrated in FIG. 1 (i.e. in the processing position), the recess 19 and the cavity 20 have an orientation in this position of the headpiece 4 which is transverse to a longitudinal axis 21 of the headpiece shaft 2, in particular at right angles thereto. The mechanical spring 30 is under pretension here (is bent in an elastic fashion).

According to the above definition, the underside of the headpiece 4 comprises in the illustrated embodiment an electrode plate 22 bearing one or more electrodes 23 (preferably in non-shiftable fashion). Arranged on the distal side 24 of the headpiece 4 is a mushroom-shaped covering cap 25 which covers the upper side of electrode plate.

The cavity 20 is situated/formed between the electrode plate 22 and the covering cap 25, the spring 30 provided therein being elastically bent by 90° in the processing position. A proximal end 26 of the spring 30 is inserted in the axial groove in the headpiece shaft 2 in a force-fitting manner and/or via a frictional fit, i.e. off-center with a transverse distance to the longitudinal axis 21. This means that the spring 30 exerting a pivot force is arranged to be offset from the pivot pin 6. In the cavity 20, however, the spring 18 is not fastened (so as to be fixed in position), but is held in movable fashion so as to allow an axial compensation or relative displacement between headpiece 4/cavity 20 and spring 30 if the headpiece 4 swivels about the pivot pin 6.

Whereas the electrode 23 may comprise several individual segments formed like a ring or the electrode 23 may be implemented as a continuous ring, it is possible to provide inserts (comprising pockets which are not shown) in addition to or instead of the electrode 23, said inserts being able to bend clips. The electrode 23 may also have a corresponding configuration. In addition, these elements may be supplied with an electrical current. In the present exemplary embodiment, the current supply to the electrode 23 is effected by means of a strand 27.

If the headpiece 4 is moved away from the headpiece shaft 2 by deliberately shifting the cross pin 6 in the direction of the arrow 5, for instance in case of exclusively or additionally using a (not illustrated) blade, such as a circular blade, which is supported in the distal end portion of the instrument shaft (not shown in further detail) so as to be axially shiftable therein, then the cross pin 6, preferably supported in the headpiece 4 in the mount so as to be not shiftable in the axial direction, moves out of the first transverse hole 11 and overcomes in this process the stretching zone 14 and the spring resistance produced by the latter, provided that a sufficiently large pushing force is exerted on the headpiece 4—and only after this process it reaches (again in a latching manner) the second transverse hole 13. Accordingly, the cross pin 6 is latched in one of the two transverse holes 11 and 13 depending on the adopted position.

If the cross pin 6 is received in the first transverse hole 11, the headpiece 4 is in the first latching position in which the distal end portion 3 of the headpiece shaft 2 is inserted in the lower-side recess of the headpiece 3 in a form-fitting manner. If the cross pin 6 is present in the second transverse hole 13, the headpiece 4 is in the second latching position. If said second latching position has been adopted, the form fit in particular between the shoulder 9 of the headpiece-side recess and the distal end portion 3 is eliminated and the mechanical spring 30 which has been under pretension up to this point in time is able to swivel the headpiece 4 in a self-acting manner, i.e. automatically, around the cross-pin 6 into the withdrawal position illustrated in FIG. 4.

As can be seen in FIG. 3, an angle α appears between the underside 28 of the headpiece 4 and the longitudinal axis 21, preferably in the range of 2.5° to 45°. A contact socket 29 connected to the strand 27 is inserted in the interior of the headpiece shaft 2 proximal relative to the distal end portion 3. Whereas FIG. 3 shows the state of the anvil assembly 1 of the anastomosis instrument in the withdrawal position, it is to be noted that the entire spring element 17, i.e. the mechanical spring 30 designed as a leaf spring, is not illustrated. It goes without saying, however, that it is also present in the withdrawal position.

FIGS. 4 to 6 illustrate the processing positions of three further, alternative anvil assemblies 1, according to the invention, of an anastomosis instrument. The construction largely corresponds to the construction of the first exemplary embodiment of the anastomosis instrument illustrated in FIGS. 1 to 3. In this respect, the details will not be repeated, but reference is made to them.

However, some differences with regard to the first exemplary embodiment shall be underlined: The exemplary embodiments of FIGS. 4 and 5 are again based on using a mechanical spring element 17, i.e. a mechanical spring 18. In both cases of the exemplary embodiments of FIGS. 4 and 5, leaf springs are employed. However, it is referred to the fact that two leaf springs are employed in the exemplary embodiment of FIG. 5; a strand according to the first exemplary embodiment and providing the energy supply of the electrode(s) is omitted. Also the exemplary embodiment illustrated in FIG. 4 does without said strand.

In this case, the leaf spring-like mechanical spring 18 may be attached to an insert 29 which is situated in the headpiece shaft and may be in (electrical) contact with the electrode 23, as it is illustrated in particular in FIG. 4.

A first leaf spring 30, as it is also illustrated in the exemplary embodiment according to FIG. 1, has a proximal end 26 firmly inserted in the headpiece shaft 2. However, it also abuts a second leaf spring or another conductor part 31 which is in electrical contact with the electrode 23 as shown in the exemplary embodiment according to FIG. 5.

As the two exemplary embodiments of FIGS. 4 and 5 do without any strands parallel to the spring, the contacting of the electrode(s) 23 is effected exclusively via the (leaf) spring(s), namely in the case of the exemplary embodiment according to FIG. 4 via a single leaf spring 30 and in the exemplary embodiment according to FIG. 5 for instance via the two leaf springs 30 and 31 (or via the spring 30 and a conductor part 31 resting against it), which contact each other in a shiftable manner.

Basically, a headpiece-side cross pin 6 is again provided here in a headpiece shaft-side (slot-type) guide 15 formed by a longitudinal slit 16, but it is also possible to resort to conical holes or (alternative) snap connections.

In the cases mentioned above, the use of the construction headpiece/headpiece shaft according to the invention (anvil assembly 1) is applied in a circular sealing element as the anastomosis instrument, whilst avoiding any clips.

The same applies for the exemplary embodiment illustrated in FIG. 6; however, other than in the exemplary embodiments discussed above, a compression spring, i.e. a coil spring 32, is arranged in an off-center, i.e. eccentric (axial) hole 33 and protrudes beyond the distal end face of the headpiece shaft 2 into the cavity 20 of the headpiece 2 and is preferably in axial abutment on a distal portion of the headpiece 4, preferably on the covering cap 25. The contacting of the electrode 23 is again effected via a strand 27, as has already been explained with respect to the exemplary embodiment of FIGS. 1 to 3.

Here too, as in all preceding exemplary embodiments, a headpiece-side cross pin 6 is inserted in a headpiece shaft-side guide 15 forming a longitudinal slit 16, namely in such a manner that it can be moved back and forth between two axially spaced latching positions by overcoming a spring-induced resistance produced by a narrowing zone 14 in the headpiece shaft. As an alternative, however, a ball-spring combination may also be used, wherein the narrowing zone is formed by a ball which can be shifted perpendicular to the shaft axis and is preloaded by a spring. As a further alternative, a configuration of a latching mechanism can be implemented which overcomes an action point.

The invention claimed is:

1. An anastomosis instrument comprising:
   a headpiece shaft which can be inserted in an instrument shaft so as to be axially shiftable therein; and
   a plate-like and/or anvil-like headpiece being axially shiftable on a distal end portion of the headpiece shaft and being supported via a cross pin between a processing position and a withdrawal position,
   the headpiece on the headpiece shaft being displaceable or shiftable from a proximally retracted first latching position in which the headpiece shaft is coupled to the headpiece in a form fit to fix the headpiece in the processing position so that it is unable to pivot, to a distally advanced second latching position in which the form fit is released in order to allow the headpiece to pivot to the withdrawal position,
   the anastomosis instrument further comprising a spring attached to the headpiece and the headpiece shaft in such a manner that it enforces a pivoting of the headpiece when the headpiece is dislocated from the first latching position to the second latching position,
   wherein the spring is eccentrically supported in the headpiece shaft so as to be transversely spaced from a longitudinal axis of the headpiece shaft, and
   wherein the cross pin is movably guided in an axially extending longitudinal slit so as to be able to be moved back and forth between the first latching position and the second latching position, the longitudinal slit being formed on the distal end portion of the headpiece shaft.

2. The anastomosis instrument according to claim 1, wherein the headpiece shaft is constructed to be resilient in an area of the longitudinal slit in its transverse direction in order to exert a spring resistance on the cross pin if the latter is shifted from its processing position to the withdrawal position along the longitudinal slit.

3. The anastomosis instrument according to claim 1, wherein the headpiece, in the second latching position, can be pivoted about the cross pin into the withdrawal position.

4. The anastomosis instrument according to claim 1, wherein the spring is shiftably supported in the headpiece or in the headpiece shaft in a groove-like recess.

5. The anastomosis instrument according to claim 1, wherein the spring is implemented as a leaf spring, leg spring, tension spring or compression spring.

6. The anastomosis instrument according to claim 1, wherein a predetermined resisting force has to be overcome during a transfer of the cross pin from the first latching position to the second latching position in the longitudinal slit of the headpiece, which is larger than expectable maximum working forces acting onto the headpiece in an axial direction during a surgical treatment.

7. The anastomosis instrument according to claim 1, wherein an activation force for triggering the first latching position is smaller than maximum working forces which are to be expected during a tissue treatment.

8. The anastomosis instrument according to claim 1, wherein the form fit is formed by an axial recess or protrusion on the headpiece, said recess or protrusion being shaped on its underside facing the headpiece shaft and in which the distal end portion of the headpiece shaft engages in a pivot-proof manner in the processing position.

9. The anastomosis instrument according claim 1, wherein the anastomosis instrument is a TFT instrument or a clip setting instrument.

10. An anastomosis instrument comprising:
    a headpiece shaft which can be inserted in an instrument shaft so as to be axially shiftable therein; and
    a plate-like and/or anvil-like headpiece being axially shiftable on a distal end portion of the headpiece shaft and being supported via a cross pin between a processing position and a withdrawal position,
    the headpiece on the headpiece shaft being displaceable or shiftable from a proximally retracted first latching position in which the headpiece shaft is coupled to the headpiece in a form fit to fix the headpiece in the processing position so that it is unable to pivot, to a distally advanced second latching position, in which the form fit is released in order to allow the headpiece to pivot to the withdrawal position,
    the anastomosis instrument further comprising a spring attached to the headpiece and the headpiece shaft in such a manner that it enforces a pivoting of the headpiece when the headpiece is dislocated from the first latching position to the second latching position,
    wherein the cross pin is movably guided in an axially extending longitudinal slit so as to be able to be moved back and forth between the first latching position and the second latching position, the longitudinal slit being formed on the distal end portion of the headpiece shaft.

11. An anastomosis instrument comprising:
    a headpiece shaft which can be inserted in an instrument shaft so as to be axially shiftable therein; and
    a plate-like and/or anvil-like headpiece being axially shiftable on a distal end portion of the headpiece shaft and being supported via a cross pin between a processing position and a withdrawal position,
    the headpiece on the headpiece shaft being displaceable or shiftable from a proximally retracted first latching position, in which the headpiece shaft is coupled to the headpiece in a form fit to fix the headpiece in the processing position so that it is unable to pivot, to a distally advanced second latching position, in which the form fit is released in order to allow the headpiece to pivot to the withdrawal position, wherein the cross pin is movably guided in an axially extending longitudinal slit so as to be able to be moved back and forth between the first latching position and the second latching position, the longitudinal slit being formed on the distal end portion of the headpiece shaft, and wherein the headpiece shaft is constructed to be resilient in the area of the longitudinal slit in its transverse direction in order to exert a spring resistance on the cross pin if the latter is shifted from its processing position to the withdrawal position along the longitudinal slit.

\* \* \* \* \*